(12) United States Patent
Bonne et al.

(10) Patent No.: US 7,003,418 B2
(45) Date of Patent: Feb. 21, 2006

(54) METHODS AND SYSTEMS FOR TEMPERATURE COMPENSATION OF PHYSICAL PROPERTY SENSORS

(75) Inventors: Ulrich Bonne, Hopkins, MN (US); David Kubisiak, Chanhassen, MN (US)

(73) Assignee: Honeywell International Inc., Morristown, NJ (US)

( * ) Notice: Subject to any disclaimer, the term of this patent is extended or adjusted under 35 U.S.C. 154(b) by 7 days.

(21) Appl. No.: 10/651,323

(22) Filed: Aug. 28, 2003

(65) Prior Publication Data

US 2005/0049805 A1 Mar. 3, 2005

(51) Int. Cl.
*G01F 1/12* (2006.01)
*G01F 1/50* (2006.01)
*G01F 25/00* (2006.01)

(52) U.S. Cl. .................. 702/100; 702/45; 702/50; 702/104; 73/1.16; 73/1.59; 73/204.19

(58) Field of Classification Search .................. 702/45, 702/47, 48, 49–51, 53, 54, 57, 85, 86, 98–100, 702/103, 104, 30, 132–134, 136–138, 140; 73/1.57, 1.16, 1.59, 204.15, 204.18, 204.19, 73/204.23, 204.25, 204.26; 374/1, 3
See application file for complete search history.

(56) References Cited

U.S. PATENT DOCUMENTS

| | | | |
|---|---|---|---|
| 4,612,895 A | 9/1986 | Kuroiwa et al. | 123/494 |
| 4,688,424 A | 8/1987 | Handtmann et al. | 73/204 |
| 4,938,061 A | 7/1990 | Carp | 73/204.19 |
| 5,161,410 A * | 11/1992 | Davey et al. | 73/204.22 |
| 5,177,696 A | 1/1993 | Bonne | 702/136 |
| 5,237,523 A * | 8/1993 | Bonne et al. | 702/100 |
| 6,019,505 A | 2/2000 | Bonne et al. | 374/40 |
| 6,184,773 B1 | 2/2001 | Bonne et al. | 338/25 |
| 6,209,402 B1 | 4/2001 | Yamada | 73/861.26 |
| 6,223,593 B1 | 5/2001 | Kubisiak et al. | 73/204.15 |

(Continued)

FOREIGN PATENT DOCUMENTS

EP 0348245 A2 12/1989

(Continued)

OTHER PUBLICATIONS

PCT Notification of Transmittal of The International Search Report and The Written Opinion of the International Searching Authorithy, or the Declaration—Date of Mailing Dec. 22, 2004.

*Primary Examiner*—Marc S Hoff
*Assistant Examiner*—Manuel L. Barbee
(74) *Attorney, Agent, or Firm*—Kris T. Frederick; Kermit D. Lopez; Luis M. Ortiz (57) ABSTRACT

Temperature compensation methods for physical property sensors are disclosed herein, based on a simple bridge circuit. An imbalance of the bridge circuit can be driven to a zero value, while a supply voltage thereof is simultaneously driven to a level required to bring the heating element to the temperature rise above ambient temperature that optimally compensates for a number of temperature-dependent effects. The heating element can be configured as a thin-film heating material. The resulting total temperature dependence of the measuring system, which includes the heating element, the bridge-circuit with amplifier and the fluid to be measured, can be reduced to a level at which the need for additional digital temperature compensation circuitry and its associated costs may be reduced.

20 Claims, 9 Drawing Sheets

U.S. PATENT DOCUMENTS

| | | | |
|---|---|---|---|
| 6,234,016 B1 * | 5/2001 | Bonne et al. | 73/204.26 |
| 6,346,703 B1 * | 2/2002 | Lee et al. | 250/338.1 |
| 6,361,206 B1 | 3/2002 | Bonne | 374/138 |
| 2003/0119197 A1 | 6/2003 | Bonne et al. | 436/149 |

FOREIGN PATENT DOCUMENTS

| | | |
|---|---|---|
| EP | 0549947 A1 | 7/1993 |
| GB | 1596648 | 8/1981 |

* cited by examiner

METHODS AND SYSTEMS FOR TEMPERATURE COMPENSATION OF PHYSICAL PROPERTY SENSORS

TECHNICAL FIELD

Embodiments generally relate to material and physical property sensors, such as fluid or solid sensors. Embodiments also relate to temperature compensation methods and systems. Embodiments additionally relate to electrical circuitry, such as Wheatstone Bridge circuits utilized in sensor applications.

BACKGROUND OF THE INVENTION

A number of approaches have been devised to measure the thermal conductivity, thermal diffusivity, specific heat and fluid velocity of a fluid or solid of interest. Typically, these and other properties are detected through the use of various types of detectors including resistive bridge type sensors.

One approach for determining thermal conductivity involves the use of a heated element in one leg of a Wheatstone Bridge. The heated element can be placed or positioned in a cavity through which the sample fluid of interest is passed. The heated element is used to introduce a series of amounts of thermal energy into the fluid of interest at various levels by varying the input voltage via alternating current, voltage or power so that the changes in dissipated power caused by changes in the thermal properties of the surrounding fluid or solid (e.g. powder) can be detected as voltage, current or resistance change signals. One of the measurable fluid properties is the thermal conductivity of the fluid.

Further to the measurement of thermally induced changes in electrical resistance, as will be discussed in greater detail below, very small and very accurate "micro bridge" or "micro membrane" semiconductor chips supporting sensors have been implemented in the context of heaters and sensors. Such sensors might include, for example, a pair of thin film sensor elements around a thin film heater element for measuring flow rates. An example of a semiconductor chip sensor configuration is disclosed U.S. Pat. No. 6,361,206, "Microsensor Housing", which issued to Ulrich Bonne on Mar. 26, 2002, and which is incorporated herein by reference. It can be appreciated that U.S. Pat. No. 6,361,206 is referenced herein for generally illustrative and background purposes only, and should not be considered a limiting feature of the present invention.

Another approach for measuring the thermal conductivity, thermal diffusivity and specific heat of a fluid involves the use of a micro bridge structure that has a heater film and at least one spaced sensor films. A pulse of electrical energy can be applied to the heater at a level and duration such that both a transient change and a substantially steady-state temperature occur at the sensor.

The thermal conductivity of the fluid of interest is determined based upon a known relation between the sensor output and the thermal conductivity at steady-state sensor temperatures. The specific heat and thermal diffusivity of the fluid of interest are determined based on a known relation among the thermal conductivity, the rate of change of the sensor output during a transient temperature change in the sensor, and the thermal diffusivity and specific heat.

A typical approach for determining the velocity of a fluid of interest is to determine the time require for a thermal wave to flow from a source heater element to a destination sensor element. By knowing the distance between the heater element and the sensor element, the velocity of the fluid can be calculated.

The thermal waves can propagate through the fluid at a rate that is dependent on the fluid velocity flowing perpendicular to the heater strip. A thermo-electric detector, spaced from one or both side of the heater, senses the thermal wave and provides a corresponding detector output signal. The velocity of the fluid is determined, at least to first order, from the time differential between the heater input signal and the detector output signal.

In many instances it may be necessary to achieve temperature compensation for fluid properties, such as thermal conductivity, viscosity, pressure, vapor concentration, and so forth. Heretofore, temperature compensation has involved digitally processing independent signals of property and temperature, preferably taken at two temperatures, and requiring a fair amount of time. Other methods, such as an orientation sensor and many of the aforementioned devices, provide no compensation at all. The ability to achieve temperature compensation properly for fluid sensors, such as the fluid sensors discussed above, and other similar sensing devices, is an important objective that has not yet been achieved. The methods and systems disclosed herein provide a solution to the lack of temperature compensation associated with current and traditional thermal property and other fluid property sensors.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide improved temperature compensation methods and systems for physical property sensors.

It is another aspect of the present invention to provide improved temperature compensation methods and systems for physical property (e.g., gas, liquid or solid) sensors.

The aforementioned aspects of the invention and other objectives and advantages can now be achieved as described herein. Temperature compensation methods and systems for physical property sensors are disclosed herein. An example of a physical property sensor is a fluid property sensor. A bridge circuit (e.g., a Wheatstone Bridge circuit) can be located on a physical property sensor substrate. Such a bridge circuit can include one or more heating elements and a plurality of resistors, including a plurality of compensating resistors thereof. An imbalance of the bridge circuit can be driven to a zero value while a supply voltage thereof is simultaneously driven to a level required to stabilize the heating element at a constant temperature rise above ambient temperature.

The heating element can comprise a thin-film heating material. A non-linear temperature coefficient of resistance of the thin-film heating material can then be dynamically compensated utilizing one or more compensating resistors of the bridge circuit. Temperature compensation can therefore be achieved in a front-end analog circuit (i.e., the bridge circuit), which can serve eliminate the need for digital circuitry and its associated cost.

BRIEF DESCRIPTION OF THE DRAWINGS

The accompanying figures, in which like reference numerals refer to identical or functionally similar elements throughout the separate views and which are incorporated in and form part of the specification, further illustrate embodiments of the present invention.

DETAILED DESCRIPTION OF THE INVENTION

The particular values and configurations discussed in these non-limiting examples can be varied and are cited merely to illustrate an embodiment of the present invention and are not intended to limit the scope of the invention.

Figure 1:
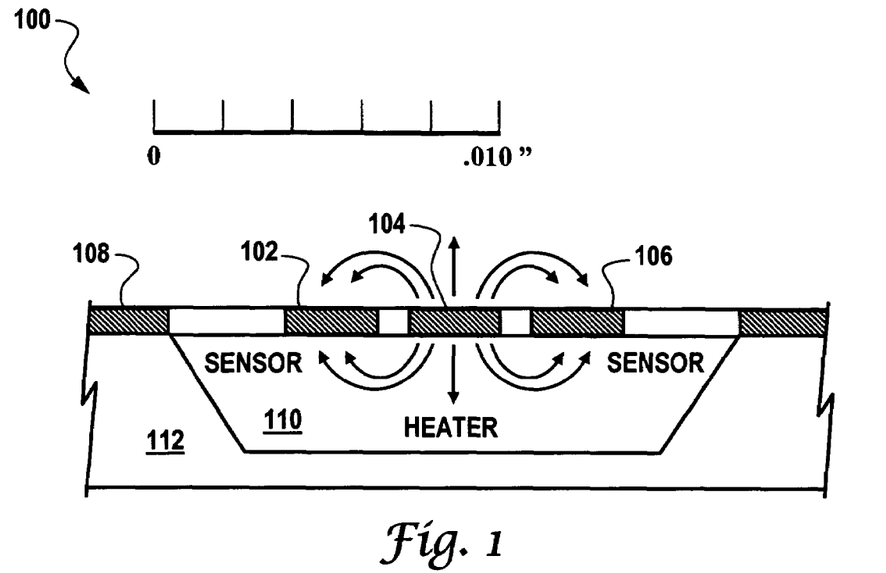
FIG. 1 illustrates a temperature compensation system for a fluid property sensor, which can be implemented in accordance with an embodiment of the present invention.

With reference now to the figures, and in particular with reference to FIG. 1, a temperature compensation system 100 for a fluid property sensor is illustrated in accordance with an embodiment of the present invention. System 100 generally includes a substrate 112 upon which sensor portions 102 and 106 may be formed over a sensor region 110 and beside a heater portion 104. The configuration of system 100 can be modified to include fewer or greater sensor portions, depending on desired implementations. Sensor portions 102 and 106 can, for example, can function as a single sensor or a plurality of individual sensors. System 100 can thus be implemented in the context of an integrated circuit (IC) chip.

Figure 2:
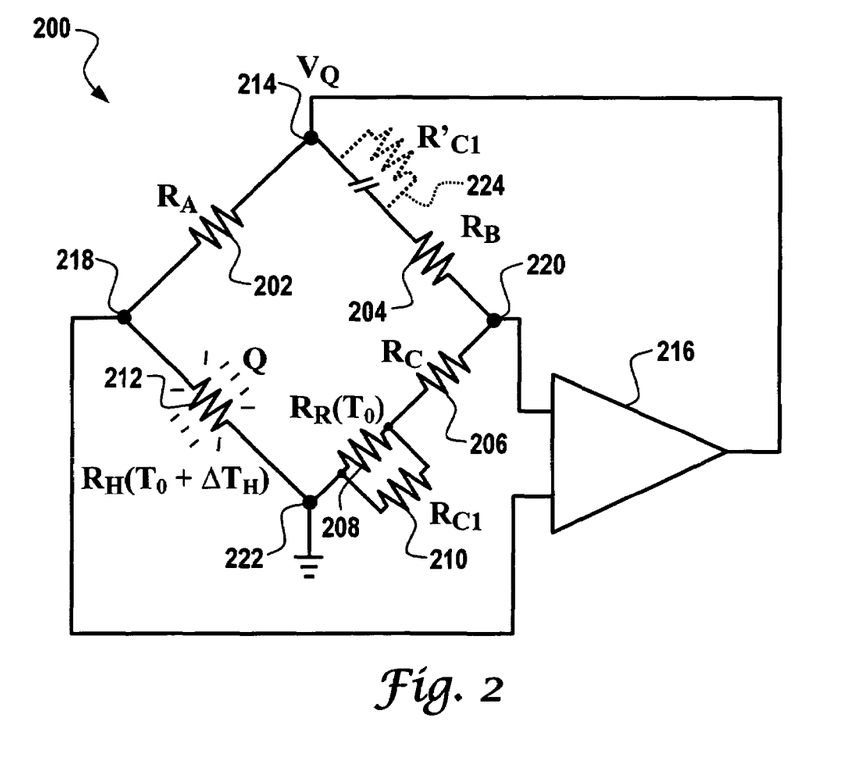
FIG. 2 illustrates a schematic electrical diagram of a micro-bridge circuit, which can be implemented in accordance with an embodiment of the present invention.

FIG. 2 illustrates a schematic electrical diagram of a micro-bridge circuit 200, which can be implemented in accordance with an embodiment of the present invention. Circuit 200 of FIG. 2 is associated with system 100 of FIG. 1. Circuit 200 comprises a heater Wheatstone bridge (WB) circuit that includes at least resistors 202, 204, 206, and 210, which are respectively also labeled in FIG. 2 as resistors $R_A$, $R_B$, $R_C$ and $R_{C1}$. Circuit 200 can be utilized to implement heater portion 104 of FIG. 1. An optional resistor 224, labeled in FIG. 2 as $R'_{C1}$ can be located between resistor 204 and resistor 202. Circuit 200 further includes an op-amp device 216 whose output is tied back between resistors 202 and 204 at a node 214, also labeled as $V_Q$.

In the illustrated approach of FIG. 2, resistors $R_A$, $R_B$, $R_C$ and $R_{C1}$ are temperature independent, but a thin-film resistance 212 ($R_H$, on the micro-bridge) and 208 ($R_R$, on the chip, i.e., system 100) are not. Resistor 210 and resistance 208 are shown parallel with each other in FIG. 2 and tied to a ground 222, along with resistance 212. The combined temperature dependencies of $R_H$, its heat dissipation via thermal conductivity and that of the reference resistor system, $[R_R+R_C+R_{C1}]$, are configured to cancel, so that $V_Q$ becomes temperature independent, which generally requires that $\Delta T_{htr}$ (T) is approximately equivalent to a constant value.

The temperature compensation methods and systems disclosed herein can be achieved utilizing a temperature compensation technique adapted to flow sensors for the measurement of fluid properties. Such a technique preferably involves a measurement of thermal conductance, which can then be correlated to parameters such as thermal conductivity, viscosity, pressure, vapor concentration orientation and/or other properties such as specific heat. Although the flow sensor depicted herein illustrates a preferred microstructure because of its established/proven commercial availability, stability, compactness, low cost, low power consumption and ruggedness (i.e., shock, vibration and overpressure), other structures are clearly possible. Other structures can benefit from the temperature compensation proposed here.

Achieving a temperature compensated output for a flow sensor can be achieved via a circuit, such as circuit 200 of FIG. 2. As depicted in FIG. 2, a configuration is presented in which the heater's Wheatstone bridge (WB) imbalance driven to zero and its supply voltage is simultaneously driven to a level needed to stabilize the heating element at the desired, constant temperature rise above ambient, $\Delta T_{htr}$, while compensating for the non-linear TCR (Temperature Coefficient of Resistance) of the thin-film heater material (e.g., Pt, FeNi, etc.) via a zero-TCR, compensating resistor, $R_c$.

In order to avoid altering the intended $\Delta T_{htr}$ at reference conditions, an additional, zero-TCR, parallel resistor 210, which is labeled as $R_{C1}$ in FIG. 2, can be provided, which brings the total reference resistance back to its original value, after increasing $R_C$ to also compensate for the temperature dependence of thermal conductivity, k. The heater WB circuit 200 of FIG. 2 represents a preferred embodiment of a temperature compensation method and/or system for property sensors. For varying methods for the measurement of k (i.e., reflecting some of the different ways for the measurement of flow) the illustrated embodiment can be characterized by several factors, including measurement of heater power, measurement of temperature field, and extrapolation to property values at reference conditions.

The measurement of heater power can be achieved under conditions in which the heater element (e.g., heater portion 104 of FIG. 1) is maintained at an approximately constant temperature rise above ambient, t. The value t can be configured to vary with ambient temperature precisely enough to compensate for the combined effects of the non-linear heater-film TCR and the temperature dependence of the thermal conductance (i.e. heater thermal power dissipation) as indicated approximately by a WB input voltage, $V_Q^2$, such that $V_Q$, which is the value to be correlated to the property of interest, then becomes precisely independent of ambient temperature.

Because each fluid has its individual temperature dependence of thermal conductivity (or of thermal conductance in the geometrical setting of the sensor), the exact elimination of $V_Q$'s temperature dependence is only achieved for the one chosen fluid. Preferably, we would choose that fluid to be one serving as reference fluid, such as "normal" air, e.g. for atmospheric pressure measurements, leak detection, gasoline vapor concentration; but one would choose methane for the determination of natural gas properties, or water for aqueous solutions, or hexadecane for fuel oils. As "normal" air one would select air at T, p, RH and $CO_2$ concentration values corresponding to averages for the intended application.

Figure 3A:
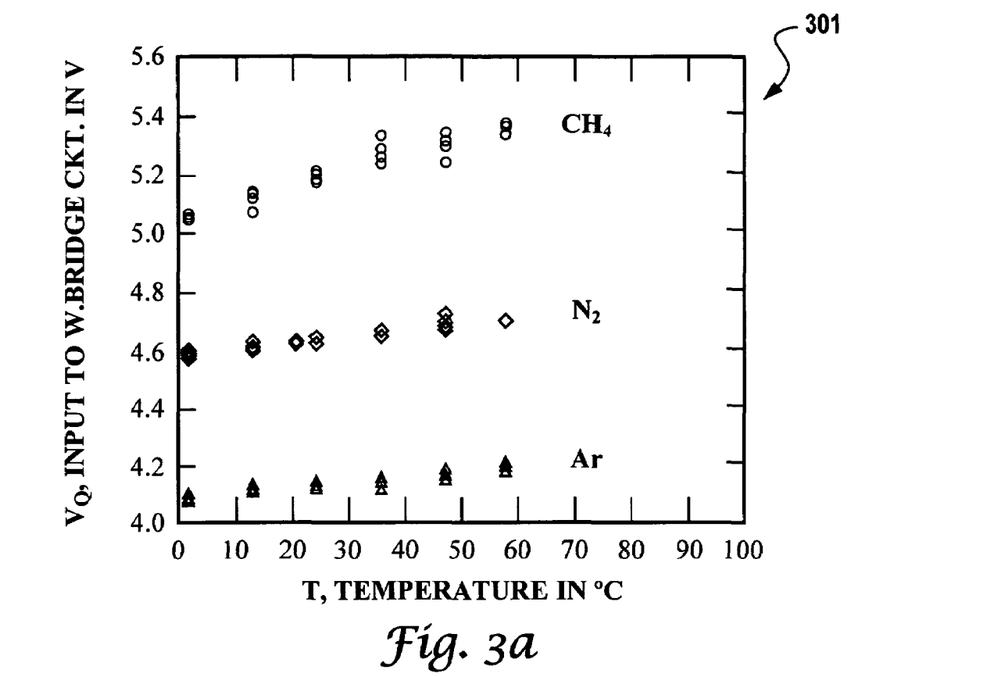
FIG. 3a illustrates a graph of temperature dependence of a sensor prior to compensation, in accordance with an embodiment of the present invention.
Figure 3B:
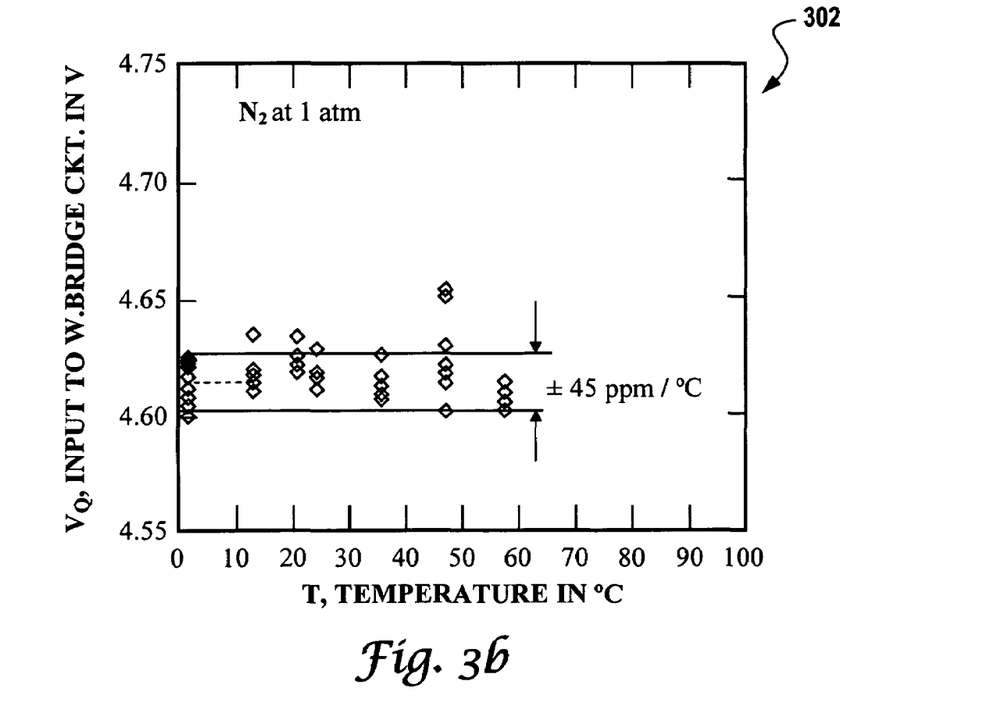
FIG. 3b illustrates a graph of temperature dependence of a sensor after compensation, in accordance with an embodiment of the present invention.

FIG. 3a illustrates a graph 301 of temperature dependence of a sensor prior to compensation, in accordance with an embodiment of the present invention. FIG. 3b illustrates a graph 302 of temperature dependence of a sensor after compensation, in accordance with an embodiment of the present invention. The data plotted in FIGS. 3a and 3b generally illustrates values, which can be obtained for three gases near atmospheric pressure after adjustment of $R_C$ to achieve constant heater temperature rise above ambient, $\Delta T_{htr}$ (FIG. 3a), and after simulating the effect of additions to $R_C$ and of $R_{C1}$ to make $V_Q$ independent of temperature for $N_2$ (FIG. 3b).

Alternative methods and systems for this measurement approach (heater power) can include, for example, operating the heater's WB at constant current (measure WP's input voltage a input power), constant voltage (measure WP's input current a input power) or constant power (measure WP's input voltage or current) excitation. Note that none of the above makes use of the sensing elements of the sensor structure.

Figure 4A:
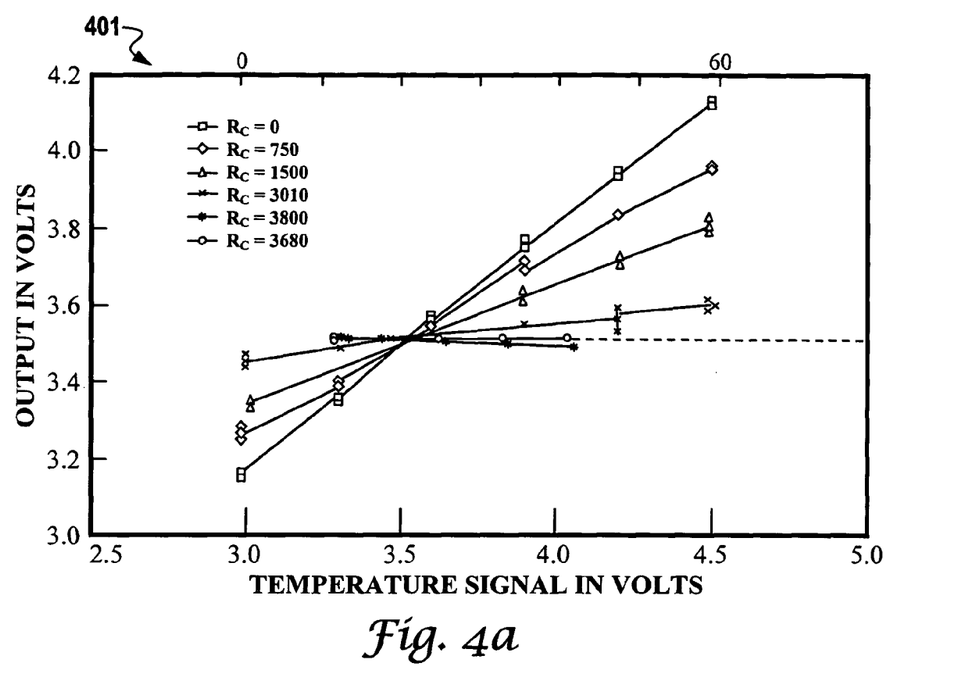
FIG. 4a illustrates a graph of temperature signals in volts versus output in volts, in accordance with an embodiment of the present invention.
Figure 4B:
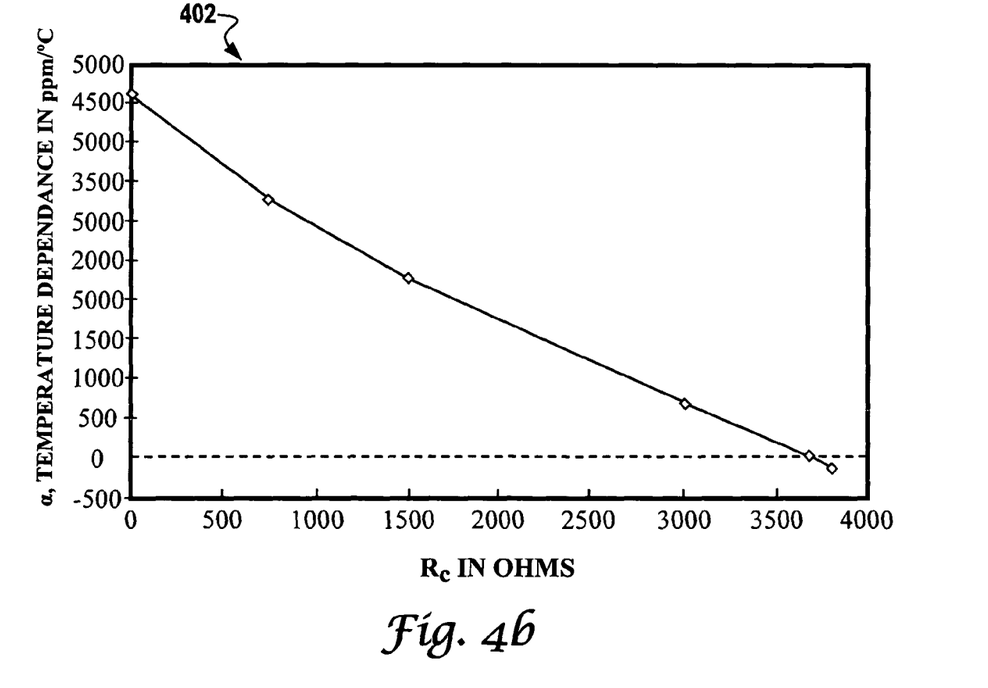
FIG. 4b illustrates a graph of temperature sensitivity of a thermal conductivity sensor versus resistance in ohms, in accordance with an embodiment of the present invention.

FIG. 4a illustrates a graph 401 of temperature signals in volts versus output in volts, in accordance with an embodiment of the present invention. FIG. 4b illustrates a graph 402 of temperature sensitivity of a thermal conductivity sensor versus resistance in ohms, in accordance with an embodiment of the present invention.

The measurement of a temperature field can be performed under conditions of constant $\Delta T_{htr}$ (preferred) or by holding the other parameters constant as above, by sensing the temperature rise above ambient of the thin-film elements (preferably the average of those two elements) adjacent to the heater. For example, graphs 401 and 402 respectively illustrate a temperature rise, expressed as a sensor's WB output voltage, $V_S$, changes as a function of the changing k value of different gases. The $R_c$ of the heater's WB is now chosen to keep $\Delta T_{htr}$ constant and the $R_c$ of the sensors WB is chosen to eliminate the temperature dependence of $V_S$, again, only for the chosen fluid.

Extrapolation to Property Value at Reference Conditions. This approach is based on either (a) Deriving and using a correlation between measured values of T and k (and possibly others such as $c_p$) and the desired value $k_o$ at reference temperature, $T_o$; (b) Measuring k at two (preferred) or more temperatures, realized by operating the heater at two temperatures (e.g. 60 and 120-C) in order to then enable extrapolation to $k_o$; this involves significant time, which may disqualify the sensor in some applications or (c) To avoid this time delay, measuring $k_1$ and $k_2$ at effective temperatures $T_1$ and $T_2$ simultaneously with two sensor chips (preferably mounted on the same alumina or TO5 substrate), so that the extrapolation of $k_o$ at $T_o$ can be made continuously and involving minimum processing time. The extrapolation may be linear, or fitted for a set of preferred fluids to a better, non-linear correlation.

$$k_o = k_1 - (T_1 - T_o)(k_2 - k_1)/(T_2 - T_1) \qquad (1)$$

Graph 401 therefore illustrates actual measurement results as $R_C$ was increased to the optimum value of 3680 Ω, and FIG. 4b a plot of the overall TCR. Graphs 401 and 402 (preferred) can be implemented via digital electronics in sensors for FFCC (feed-forward combustion control) demonstrations.

Figure 5:
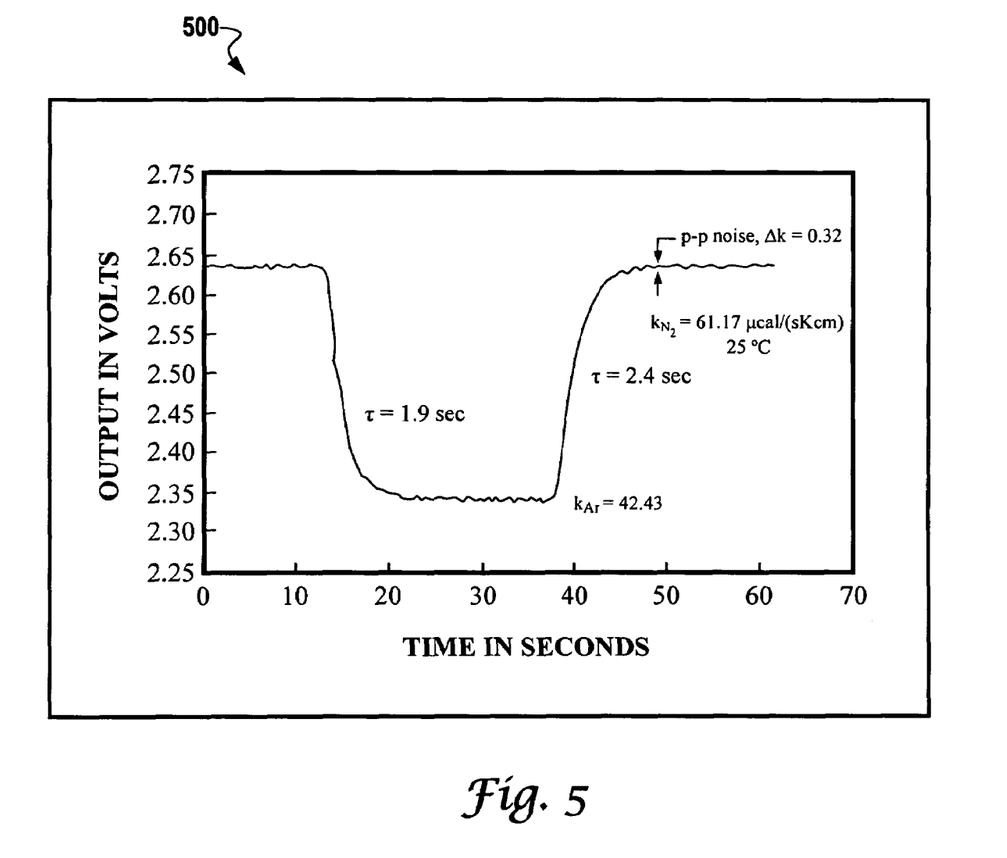
FIG. 5 illustrates a graph of purge response time of a thermal conductivity sensor, in accordance with an embodiment of the present invention.

FIG. 5 illustrates a graph 500 of purge response time of a thermal conductivity sensor, in accordance with an embodiment of the present invention. Graph 500 generally depicts how fast a sensor implemented in accordance with an embodiment of the present invention can respond to a change in gas property ($N_2$ to Argon), in spite of being held in a recessed cavity.

Figure 6:
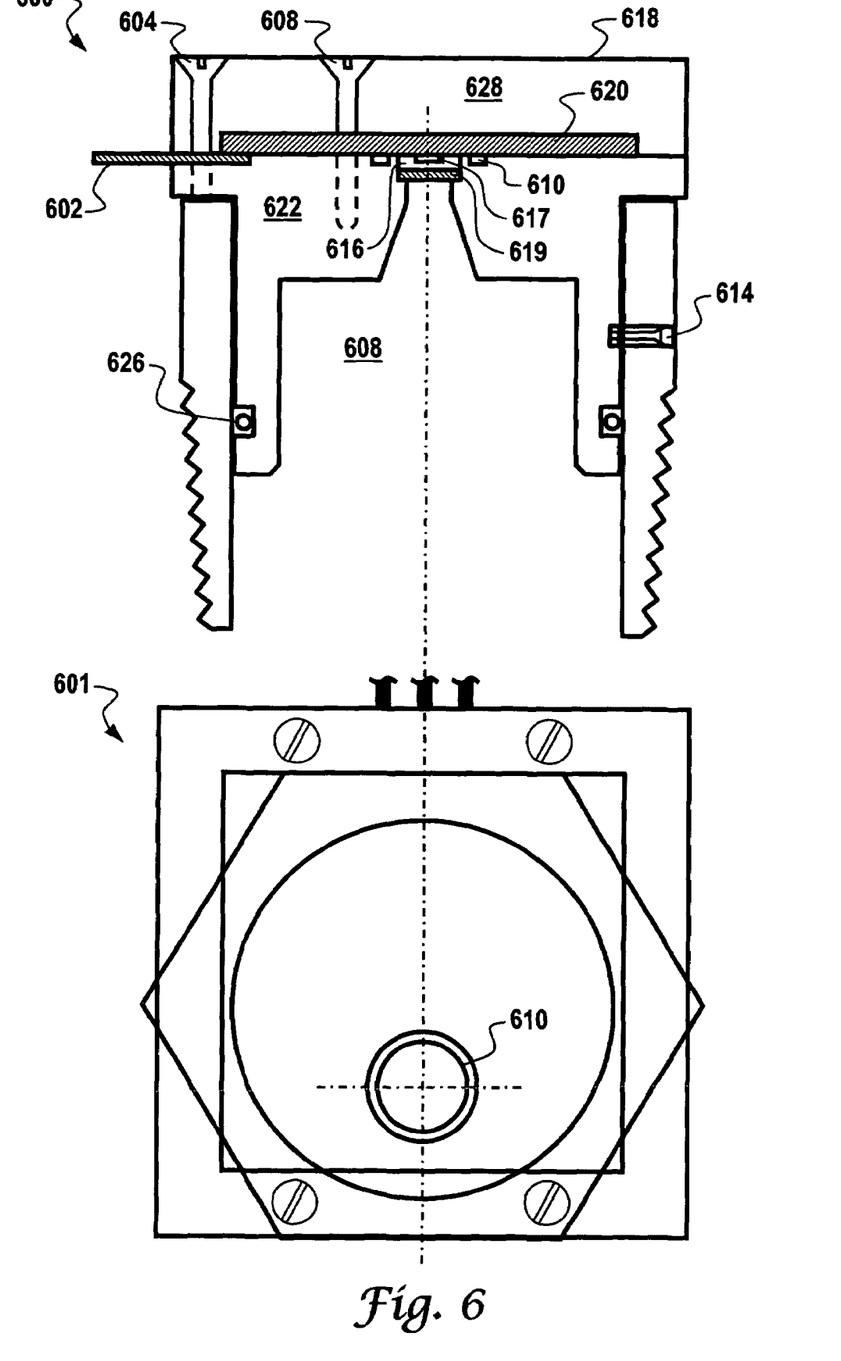
FIG. 6 illustrates a physical property sensor package holding an alumina substrate, which holds a flow sensor chip, which can be implemented in accordance with an embodiment of the present invention.

FIG. 6 illustrates a physical property sensor package 600 holding an alumina substrate, which holds a flow sensor chip, which can be implemented in accordance with an embodiment of the present invention. An O-Ring 610 surrounds an integrated circuit (IC) chip 617 to provide a gas-tight seal thereof. Sensor package 600 additionally includes holding screws 604 and 608, a housing 618 that can be constructed from metal, and an alumina substrate 620. Sensor package 600 also includes I/O (input/output) leads 602 and at least one hex nut 614.

A protective screen 619 also serves to provide a protective barrier against fluid 608. Note that chip 617 of FIG. 6 is analogous to the IC chip or system 100 of FIG. 1 and circuit 200 of FIG. 2. Sensor package 600 additionally includes a package portion 622, which seals fluid 608 via one or more O-rings 610 around the chip 617, while ring 626 (e.g., approximately 1.5" OD) keeps fluid 608 from leaking out of and past package portion 622. Note that a cover portion 618 can be implemented as a part that is separate from package portion 622 and can be held together via the screws 604 and 608, which can be located around the ceramic chip 617 and the alumina substrate 620. Note that the chip 617 can be, for example, approximately 1.7×1.7 mm in size, on a 1×1" ceramic substrate.

Figure 7:
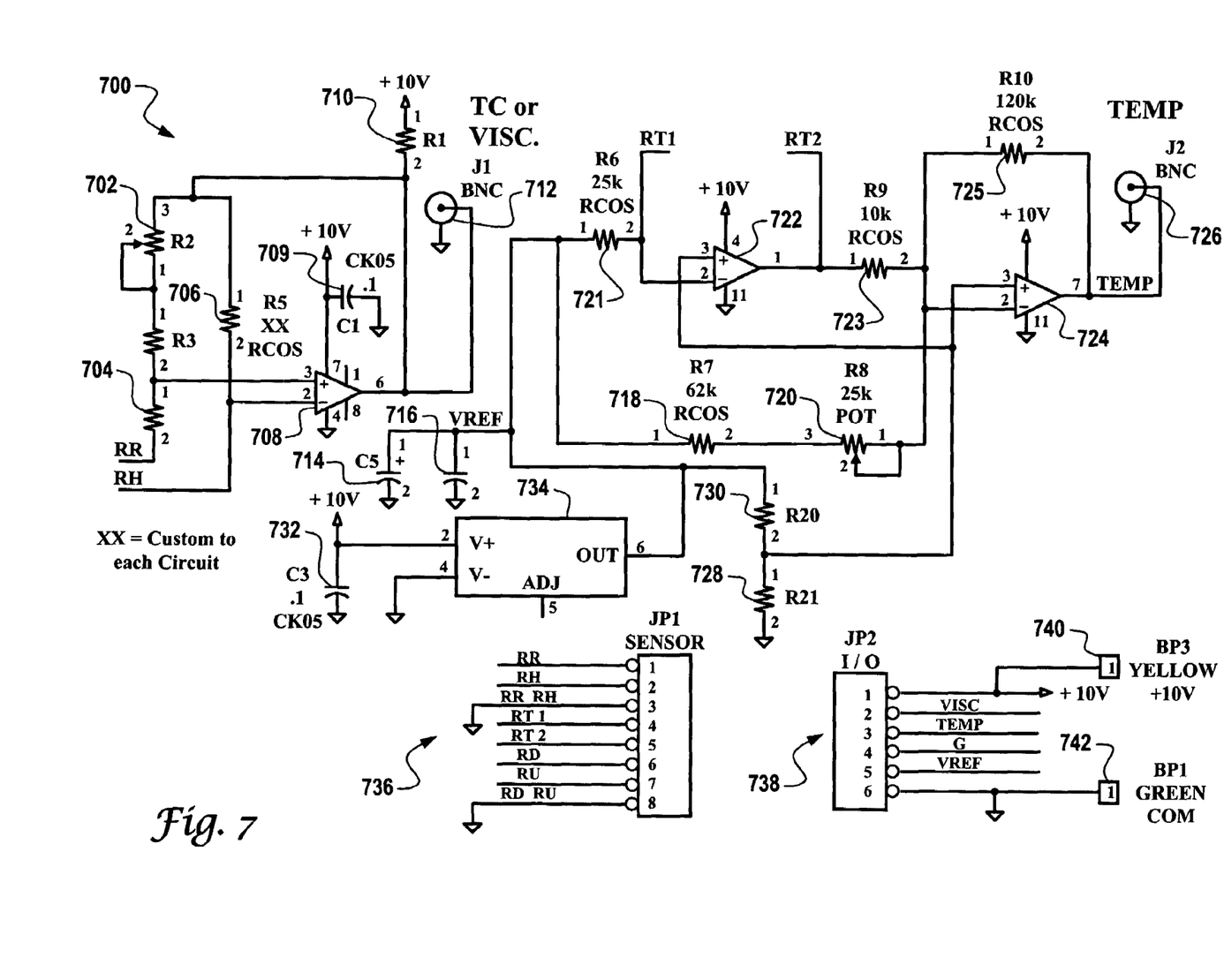
FIG. 7 illustrates an electronic circuit for a temperature compensated thermal conductivity sensor or a viscosity sensor, along with an optional temperature sensor, which can be implemented in accordance with an embodiment of the present invention.

An electronic circuit diagram of the configuration depicted in FIG. 6 is presented in FIG. 7. FIG. 7 generally illustrates an electronic circuit 700 for a temperature compensated thermal conductivity sensor or a viscosity sensor, along with an optional temperature sensor, which can be implemented in accordance with an embodiment of the present invention. Circuit 700 generally includes a resistor 702, which is connected to a resistor 704. Resistors 702 and 704 are generally located in parallel with a resistor 706. Circuit 700 additionally includes an amplifier 708, which is connected to a capacitor 709. An output of amplifier 708 is connected to a resistor 710 and a TC or viscosity detector 712. Circuit 700 also includes an amplifier 722 having at least one input connected to a resistor 721.

Resistor 721 can be further connected to a resistor 718 and parallel capacitors 714 and 716. Resistor 718 is connected in series with a POT resistor 720, which in turn is connected to a resistor 723 and a resistor 725. The resistor 723 is also connected to the output of amplifier 724. Resistor 725 is also tied to an output of amplifier 724, which is further tied to a temperature detector or sensor 726. A resistor 728 is connected in series with a resistor 730, which in turn can be connected to parallel capacitors 714 and 716. Additionally, resistor 730 and capacitors 714 and 716 can be connected to a voltage reference 734. The voltage reference 734 can be, for example, approximately +5V.

It can be appreciated, however, that this is only an illustrative example and that other voltage reference values are possible. A positive voltage (V+) input of voltage reference 734 can be tied to a capacitor 732, while a negative voltage of voltage reference 734 can be tied to ground. A micro bridge sensor 736 can also be implemented in accordance with circuit 700. Additionally, a header 738 (i.e., power supply input, signal voltage output) can also be implemented in association with a power supply input 740, whose value can be, for example, approximately +10V. A common power supply 742 can additionally be implemented in accordance with circuit 700. Common power supply 742 provides a voltage of approximately +10V.

In some applications demanding high-accuracy and well-compensated thermal conductivity output, it is necessary to eliminate also the residual influence of temperature on the sensor output signal after the analog compensation. For example, it may be necessary to eliminate a large fraction of this dependence, but doing so may limit residual TCR mismatches in the electronic components of the sensor circuit. To reduce this residual temperature effect, the addition of a temperature sensor is proposed, so that in a calibration run with the selected reference fluid (e.g. nitrogen, dry air or a stoichiometric mixture of fuel gas and air), the deviation, dV, from a constant reference output voltage, $V_o$, can be recorded as a function of temperature, T.

At a temperature, $T=T_o$, for example, the following deviation can occur: dV=0. During actual measurement, the values V and T can be measured, and the proper correction value, dV, can be interpolated from listed data so that the corrected sensor output, $V_{out}=V+dV(T)$ can be obtained and converted to thermal conductivity, k, by way of an individually derived $k(V_{out})$ function. Such a function or value can be achieved by performing a minimal number of measurements with pure gases of known k(T) values, such as $CH_4$, $N_2$ and Argon, with k values at, for example, 1 atm and 15° C. of 79.69081, 59.58516 and 41.2435 μcal/(sKcm), respectively. Once k has been determined for a chosen reference temperature (e.g. 15° C.), regardless of the actual ambient temperature by virtue of the completed temperature compensations, other fluid properties of interest, f(k), can be determined, independently of each sensor because f(k) is universal.

If in addition to a temperature sensor, also an ambient pressure sensor signal is available, then pressure compensation can be implemented via a method very similar to the look-up table method, just described, to also minimize the pressure dependence. Calculated and measured (noise and signal levels) sensor specifications can indicate, for the example, the use of a thermal conductivity sensor as a rough butane-air stoichiometry sensor to measure directly the mass A/F ratio or its normalized λ-value. The pressure dependence, while small in terms of its influence on k(λ) or k(A/F), could be made even smaller and thus reduce the overall error of the T and p-compensated output signal.

Similarly, the availability of specific humidity and other gas property (such as gas density, specific heat and viscosity) sensor signals could be used to reduce the errors introduced by changes in ambient humidity and in the average composition of the fluid, which may have unique and detracting influences on the intended thermal conductivity measurement.

Figure 8:
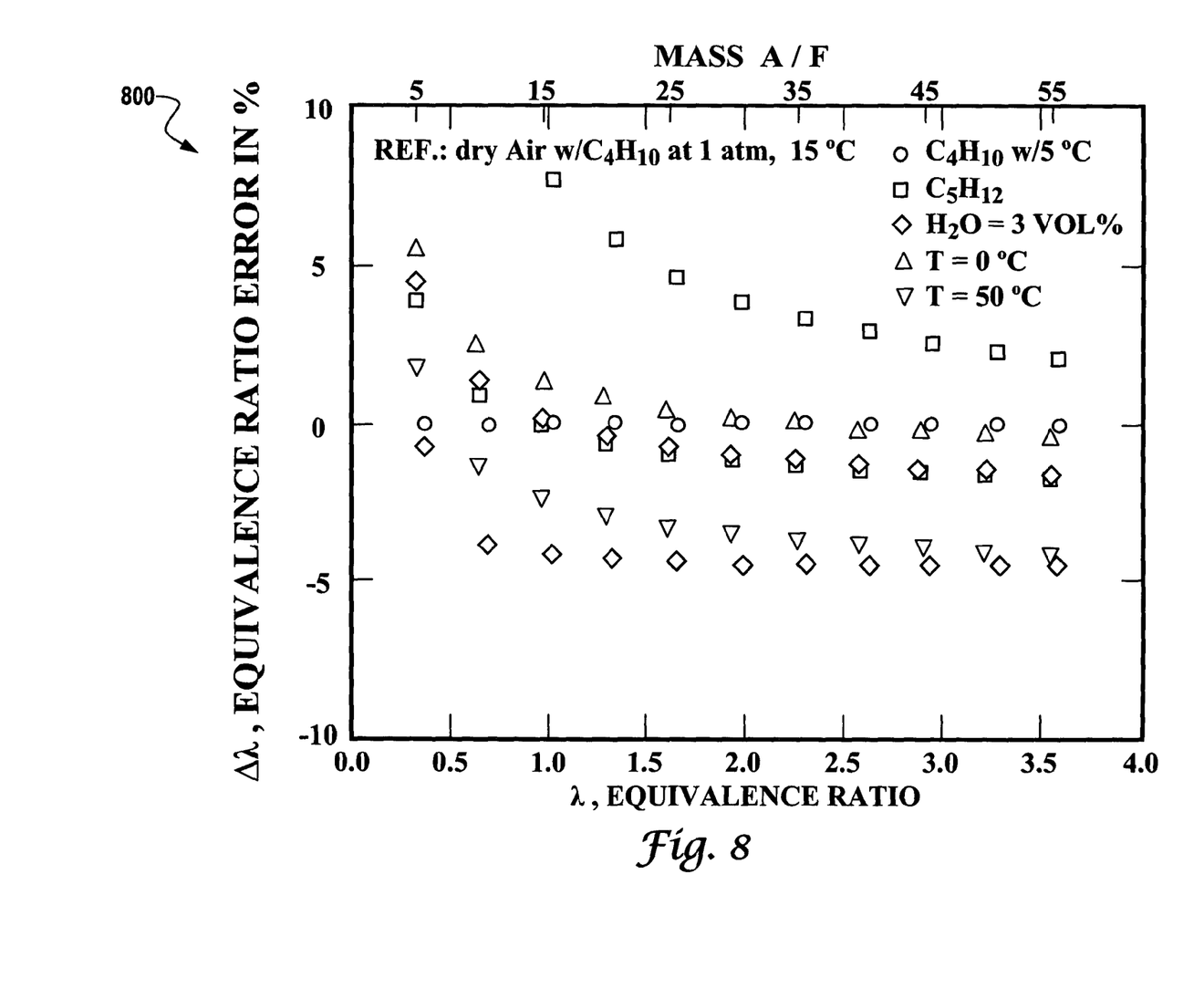
FIG. 8 illustrates a graph indicating a ratio error resulting from measurement with a compensated thermal conductivity sensor under parametric variation, in accordance with an embodiment of the present invention.
Figure 9:
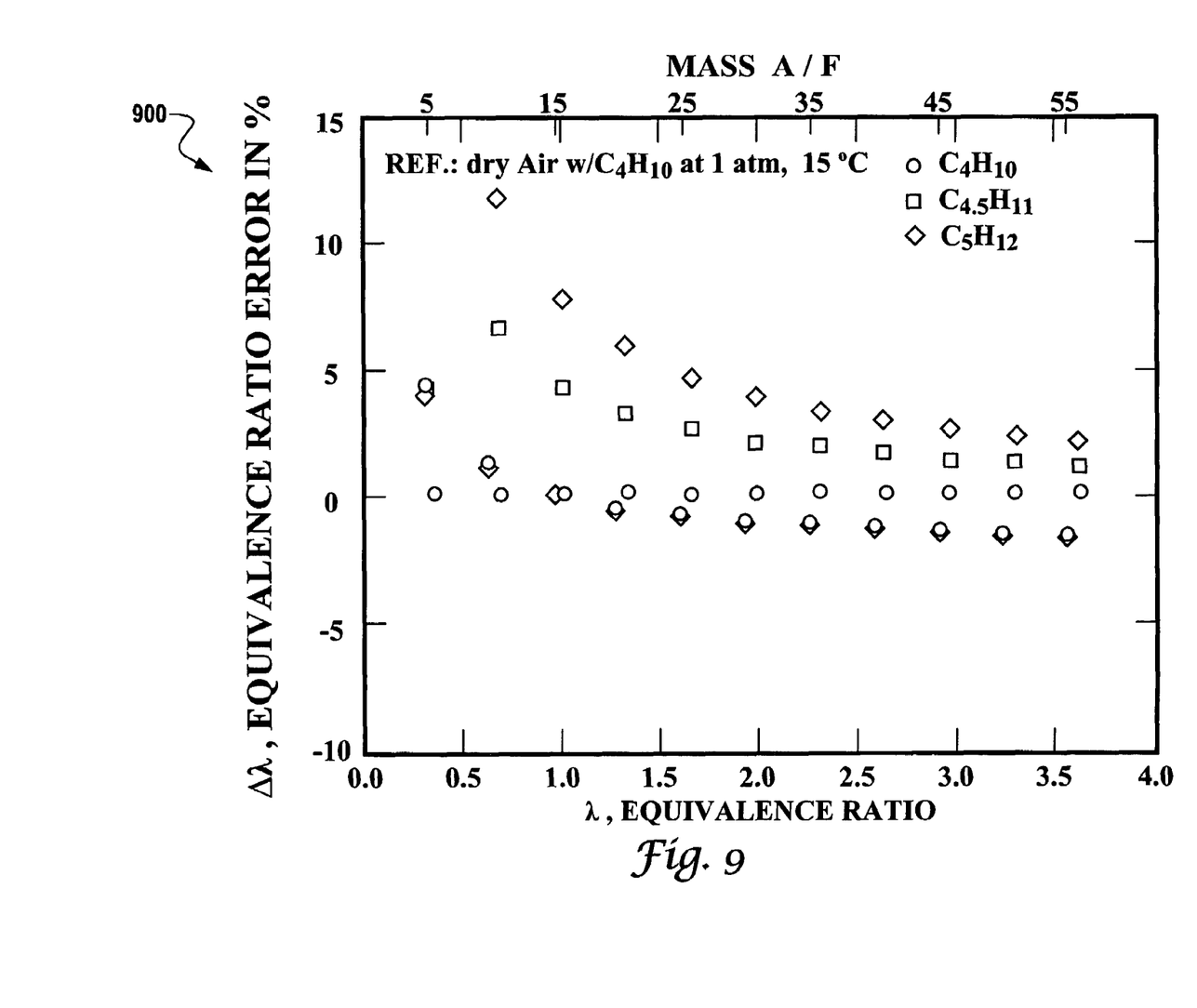
FIG. 9 illustrates a graph indicating a ratio error resulting from measurement with a compensated thermal conductivity sensor under HC-type variations, in accordance with an embodiment of the present invention.
Figure 10:
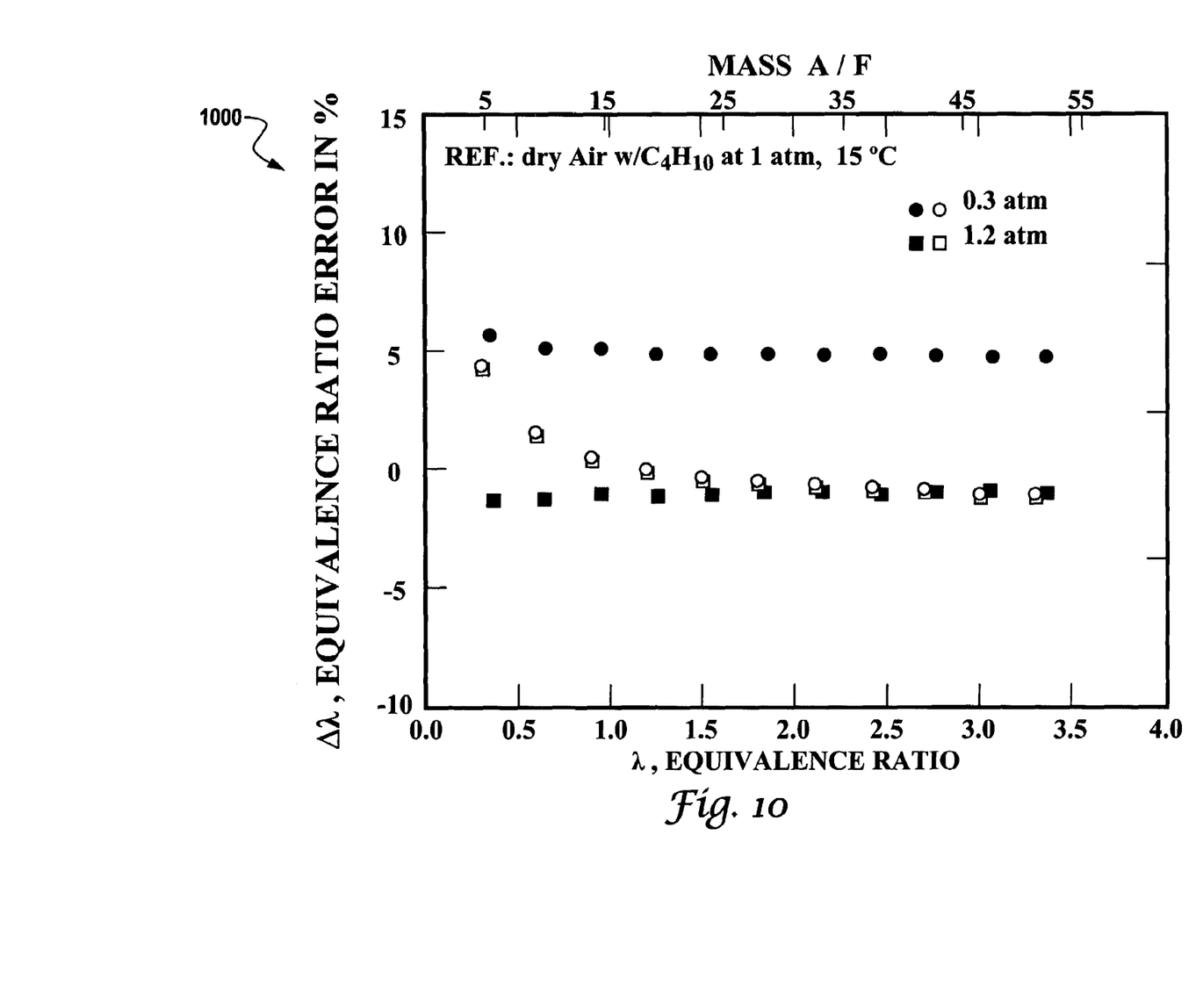
FIG. 10 illustrates a graph indicating a ration error resulting from measurement with a compensated thermal conductivity sensor under pressure variations, in accordance with an embodiment of the present invention.

FIG. 8 illustrates a graph 800 indicating a ratio error resulting from measurement with a compensated thermal conductivity sensor under parametric variation, in accordance with an embodiment of the present invention FIG. 9 illustrates a graph 900 indicating a ratio error resulting from measurement with a compensated thermal conductivity sensor under HC-type variations, in accordance with an embodiment of the present invention. FIG. 10 illustrates a graph 1000 indicating a ration error resulting from measurement with a compensated thermal conductivity sensor under pressure variations, in accordance with an embodiment of the present invention.

Graphs 800, 900 and 1000 illustrate the computed influence of humidity (0 and 3 vol. %) at various λ-values, of replacing butane by pentane or by a 50-50 mixture of the two, and of ambient pressure at the sensor location. If the desired maximum total uncertainty of the λ-measurement is ±10% of λ, then FIGS. 8–10 describe the merits of the simultaneous measurement of temperature (because we have measured the residual TCk (temperature coefficient of k) to be equivalent to 9% of λ), humidity and pressure. With these measurements and the resulting ability to reduce the individual effects of temperature, humidity and/or pressure, we can then reduce the total k-sensor output error.

Whether a basic analog k-measurement method is augmented by the addition of a microprocessor to process the various look-up table steps as an integral feature of the sensor functions, or to process these steps with the help of a microprocessor residing elsewhere is left to the discretion of the system designer.

An additional object and practical matter of is to (1) suggest the use of range mean values of disturbance variables such as humidity, pressure and fluid composition, as reference fluid conditions (rather than the ones shown in FIGS. 8–10); and (2) to reduce the cost of calibration by allowing the use of simple fluids, and not especially tightly controlled (but accurately measured!!) reference conditions for calibration, whereby the deviation from the ideal reference fluid and condition is incorporated into the ideal calibration curve via computed sensor output "deltas".

A number of advantages can accrue from implementations of the temperature compensation embodiments described herein. For example, as indicated earlier, the use of a look-up table of dV(T) data can be implemented, such that the data is added to obtain a computed and compensated readout $V_{out}=V+dV(T)+\ldots$, to further reduce the residual temperature compensation error. Additionally sensors of the fluid's humidity, pressure and/or additional properties can enable the stepwise reduction of the corresponding, undesirable influences on the sensor's output, and to thus increase its accuracy. Also, the relaxation of the calibration conditions due to the use of appropriate sensors and look-up tables can enable a cost reduction in the calibration and thus in the overall manufacturing costs.

The use of a look-up table not only can increase the accuracy of the ultimate thermal conductivity readout $k(V_{out})$, but can also relieve the accuracy requirement of the analog temperature compensation, and thus reduces the calibration and fabrication costs, by reducing the effort to match the TCRs of its circuit elements.

The ability to productive thermal conductivity sensors based on a mass air flow sensor chip, and its correlations to other properties of gases and liquids can significantly enhance with temperature-compensated sensors, as enabled via the methods and systems described herein. A number of applications are possible via implementations of embodiments of the present invention. For example, compensation for gasoline vapor concentration sensing is one application, which can result in a low-cost means for such compensation. Many designers do not want to deal with two sensor outputs, k and T, and also to work out their own temperature compensations.

Digitally; such compensation can be crucial in vapor sensing implementations because the vapor concentration induced change in k is generally smaller than that induced by temperature over the range of outdoor temperatures. On the other hand, some designers may insist on an uncompensated output, with a temperature signal thereof, when proper control of their process depends on the actual, absolute value of the property, such as for example, the viscosity of the ink in the ink-jet printer.

In general, a first temperature compensation method for physical property sensors (in a zero or low flow environment), can be implemented which is based on an adaptation of methods and systems for thermal mass air flow microsensors. Such methods or systems may or may not involve altering a set $\Delta T_{htr}$, and can generally entail, as indicated in FIG. 2, adjusting at least one resistor, $R_c$ of the heater WB, such that (for a preferred analog circuit embodiment) the temperature dependence of $V_Q$ disappears at least for one chosen reference fluid. Adjustment of $R_{C1}$ or $R_{C1}'$ may be required to maintain the desired $\Delta T_{htr}$ value.

A second temperature compensation method and/or system for physical property sensors, is based on at least two sequential (e.g., with one sensor or simultaneous with two sensors) measurements of $V_Q$, but involves different microthermal environments of the sensor(s) by changing at least one resistor in at least one of the reference legs of the heater's WB. The two values of $V_Q$ can then be related to values of k, which are thereafter converted to the temperature-compensated value, $k_o$, via equation (1) indicated herein or via its non-linear equivalent, or via an equivalent in which the two values of $V_Q$ is inserted directly, instead of the two k values.

Based on the foregoing, it can be appreciated that embodiments of the present invention are directed toward a physical property sensors and the temperature compensation of such physical property sensors. A physical property sensor, as indicated herein, can detect physical properties of materials such as gases, liquids, or solids (e.g., powder). Other physical properties, which can be detected in accordance with embodiments of the present invention can include, for example, thermal conductivity, specific heat, compressibility, octane number, heating value, speed of sound, viscosity, and the like. Embodiments can thus be implemented, which measure the thermal conductivity, thermal diffusivity, specific heat and/or fluid velocity of a fluid or solid According to embodiments of the present invention, a technique is presented in which a compensating resistor is optimized in order to minimize output signal (i.e., certain bridge voltages) variations versus ambient temperature. This optimization is therefore automatically compensated for temperature dependencies (i.e., linear or non-linear) of heater, circuit components and the material to be measured. Such compensation is optimal only for the selected material, typically air or water.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is therefore not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A temperature compensation method for a physical property sensor, said method comprising the steps of:
   locating a bridge circuit on a physical property sensor substrate wherein said bridge circuit comprises a plurality of components, including at least one heating element and a plurality of resistors, including a plurality of compensating resistors, wherein said plurality of compensating resistors includes a temperature independent resistor for compensating a temperature coefficient of resistance of said at least one heating element;
   simultaneously driving an imbalance of said bridge circuit to a zero value and a supply voltage thereof to a level required to stabilize said heating element at a required temperature rise above an ambient temperature, wherein said heating element comprises a thin-film heating material,
   adjusting the resistance value of said temperature independent resistor to compensate said temperature coefficient of resistance of said heating element(s); and
   dynamically compensating for a temperature coefficient of resistance of said thin-film heating material and a temperature dependence of said plurality of resistors and said heating element(s) of said bridge circuit components and a temperature dependence of a physical property thereof, utilizing said plurality of compensating resistors of said bridge circuit.

2. The method of claim 1 further comprising the step of configuring said bridge circuit to comprise a Wheatstone Bridge circuit.

3. The method of claim 1 further comprising the step of modifying said bridge circuit such that said plurality of compensating resistors includes one other temperature independent resistor, and
   adjusting the value of said other temperature independent compensating resistor such that, for said adjusted resistance value of said temperature independent resistor, said heating element is maintained at said required temperature rise above said ambient temperature.

4. The method of claim 1 further comprising the step of increasing a resistance value of said temperature independent resistor to compensate for a temperature dependence of a physical property value.

5. The method of claim 4, wherein said physical property value comprises a value of at least one of the following: thermal conductivity, specific heat, compressibility, octane number, heating value, speed of sound, and viscosity.

6. The method of claim 1 further comprising the steps of:
   measuring a heater power of said heating element at an approximately constant temperature rise above said ambient temperature, wherein said approximately constant temperature rise varies with said ambient temperature to compensate for a combined effect of said thin-film heating material, said components of said bridge circuit, and a fluid property to be measured by said physical property sensor.

7. The method of claim 1 further comprising the step of minimizing a change in a bridge voltage of said bridge circuit as said ambient temperature is varied over a required range by an optimal choice of a value of said temperature independent resistor.

8. The method of claim 7 further comprising the step of selecting said bridge voltage as a supply voltage generated by an amplification of a bridge circuit imbalance, such that said bridge voltage serves as a sensor output signal of said physical property sensor.

9. The method of claim 1 wherein said bridge circuit comprises a front-end analog circuit of said physical property sensor.

10. The method of claim 1 wherein said physical property sensor comprises a gas property sensor.

11. The method of claim 1 wherein said physical property sensor comprises a liquid property sensor.

12. The method of claim 1 wherein said physical property sensor comprises a solid property sensor.

13. A temperature compensation method for a physical property sensor, said method comprising the steps of:
locating a bridge circuit on a physical property sensor substrate wherein said bridge circuit comprises a plurality of components, including at least one heating element and a plurality of resistors, including a plurality of compensating resistors, wherein said plurality of compensating resistors includes first and second temperature independent resistors;
simultaneously driving an imbalance of said bridge circuit to a zero value and a supply voltage thereof to a level required to stabilize said heating element at a required temperature rise above an ambient temperature, wherein said heating element comprises a thin-film heating material;
dynamically compensating for a temperature coefficient of resistance of said thin-film heating material and a temperature dependence of said plurality of of resistors and said heating element(s) of said bridge circuit components and a temperature dependence of a physical property thereof, utilizing said compensating resistors of said bridge circuit, wherein said physical property includes at least one of the following: thermal conductivity, specific heat, compressibility, octane number, heating value, speed of sound, and viscosity;
increasing a resistance value of said first temperature independent resistor to compensate for a temperature dependence of a physical property value, wherein said physical property value comprises a value of at least one of the following: thermal conductivity, specific heat, compressibility, octane number, heating value, speed of sound, and viscosity;
adjusting the resistance value of said second temperature independent resistor such that, for said increased resistance value of said first temperature independent resistor, said heating element is maintained at said required temperature rise above said ambient temperature;
minimizing a change in a bridge voltage or said bridge circuit as said ambient temperature is varied over a required range by an optimal choice of a value of said first temperature independent resistor; and selecting said bridge voltage as a supply voltage generated by an amplification or a bridge circuit imbalance, such that said bridge voltage serves as a sensor output signal of said physical property sensor.

14. A temperature compensation system for a physical property sensor, comprising:
a bridge circuit comprising a plurality of components, including at least one heating element comprising a thin-film heating material and a plurality of resistors, including a plurality of compensating resistors, wherein said plurality of compensating resistors includes a temperature independent resistor, the resistance value of said temperature independent resistor being adjusted to compensate for a temperature coefficient of resistance of said at least one heating element;
a physical property sensor substrate wherein said bridge circuit is located on said physical property sensor substrate and wherein an imbalance of said bridge circuit is driven to a zero value while a supply voltage thereof is simultaneously driven to a level required to stabilize said heating element at a required temperature rise above an ambient temperature; and
a compensator for dynamically compensating for at a temperature coefficient of resistance of said thin-film heating material and a temperature dependence of said plurality of said resistors and said heating element(s) of said bridge circuit components and a temperature dependence of a physical property thereof, wherein said compensator comprises said plurality of compensating resistors of said bridge circuit.

15. The system of claim 14 wherein said bridge circuit comprises a front-end analog circuit of said physical property sensor and wherein said bridge circuit further comprises a Wheatstone Bridge circuit.

16. The system of claim 14 wherein said plurality of compensating resistors include at least one other temperature independent resistor, the resistance value of said other temperature independent resistor being adjusted such that, for said adjusted resistance value of said temperature independent resistor, said heating element is maintained at said required temperature rise above said ambient temperature.

17. The system of claim 14 wherein a resistance value of said temperature independent resistor is increased to compensate for a temperature dependence of a physical property value.

18. The system of claim 17, wherein said physical property value comprises a value of at least one of the following: thermal conductivity, specific heat, compressibility, octane number, heating value, speed of sound, and viscosity.

19. The system of claim 14 wherein a heater power or said heating element is measurable at an approximately constant temperature rise above said ambient temperature, wherein said approximately constant temperature rise varies with said ambient temperature to compensate for a combined effect of said thin-film heating material, said components of said bridge circuit, and a fluid property to be measured by said physical property sensor.

20. The system of claim 16 wherein said temperature independent resistor is arranged in series with a temperature dependent compensating resistor and wherein said other temperature independent resistor is arranged in parallel with said temperature dependent compensating resistor.

* * * * *